(12) United States Patent
Chang et al.

(10) Patent No.: US 10,379,075 B2
(45) Date of Patent: Aug. 13, 2019

(54) SAMPLE COLLECTION DEVICE AND MANUFACTURING METHOD THEREOF

(71) Applicant: Materials Analysis Technology Inc., Hsinchu County (TW)

(72) Inventors: Pin Chang, Hsinchu (TW); Hung-Jen Chen, Hsinchu (TW)

(73) Assignee: Materials Analysis Technology Inc., Hsinchu County (TW)

( * ) Notice: Subject to any disclaimer, the term of this patent is extended or adjusted under 35 U.S.C. 154(b) by 355 days.

(21) Appl. No.: 15/173,731

(22) Filed: Jun. 6, 2016

(65) Prior Publication Data
US 2017/0292927 A1    Oct. 12, 2017

(30) Foreign Application Priority Data

Apr. 11, 2016   (TW) .............................. 105111188 A

(51) Int. Cl.
| | |
|---|---|
| *G01N 27/27* | (2006.01) |
| *B01L 3/00* | (2006.01) |
| *C25D 17/00* | (2006.01) |
| *G01N 27/447* | (2006.01) |
| *H01J 37/20* | (2006.01) |
| *C25D 21/12* | (2006.01) |

(52) U.S. Cl.
CPC .............. *G01N 27/27* (2013.01); *B01L 3/508* (2013.01); *B01L 3/5027* (2013.01); *C25D 17/00* (2013.01);
(Continued)

(58) Field of Classification Search
CPC .............. G01N 27/27; G01N 27/44791; G01N 27/44704; H01J 37/20; B01L 3/508;
(Continued)

(56) References Cited

U.S. PATENT DOCUMENTS 8,059,271 B2   11/2011  Marsh et al.
9,087,848 B2    7/2015  Leontiev et al.
(Continued)

FOREIGN PATENT DOCUMENTS

CN       106289929        1/2017
CN       106290430 A  *  1/2017  ............. G01N 23/22
(Continued)

OTHER PUBLICATIONS

"Office Action of Japan Counterpart Application," dated Feb. 15, 2018, p. 1-p. 6.
(Continued)

*Primary Examiner* — J. Christopher Ball
(74) *Attorney, Agent, or Firm* — JCIPRNET

(57) ABSTRACT

A sample collection device includes two substrates and a spacer. The two substrates are disposed oppositely. Each substrate has a first surface, a second surface opposing to the first surface, a first recess and at least one second recess. The two substrates are arranged with the first surfaces facing each other, and the first and second recesses are respectively located on each first surface. The first recesses of the substrates jointly form a first channel, and the second recesses of the substrates jointly form a second channel connected to the outside of the sample collection device. The first channel and the second channel are interconnected. The spacer is disposed between the two first surfaces for bonding and fixing the two substrates. A sample containing space is formed between the two substrates and the spacer. The sample containing space includes the first chancel and the second channel. In addition, a manufacturing method of the sample collection device is also provided.

16 Claims, 17 Drawing Sheets

(52) U.S. Cl.
CPC ........ *G01N 27/44791* (2013.01); *H01J 37/20*
(2013.01); *B01L 2300/0627* (2013.01); *B01L
2300/0645* (2013.01); *B01L 2300/0809*
(2013.01); *B01L 2300/0861* (2013.01); *B01L
2300/0877* (2013.01); *B01L 2300/12*
(2013.01); *B01L 2300/18* (2013.01); *B01L
2300/1827* (2013.01); *C25D 21/12* (2013.01);
*G01N 27/44704* (2013.01)

(58) Field of Classification Search
CPC ........... B01L 3/5027; B01L 2300/0645; B01L
2300/0627; B01L 2300/1827; B01L
2300/0877; B01L 2300/0809; B01L
2300/0861; B01L 2300/12; B01L
2300/18; C25D 21/12; C25D 17/00
See application file for complete search history.

(56) References Cited

U.S. PATENT DOCUMENTS

| | | |
|---|---|---|
| 2008/0135778 A1 | 6/2008 | Liu et al. |
| 2012/0043209 A1 | 2/2012 | Liu et al. |
| 2013/0264476 A1 | 10/2013 | Damiano, Jr. et al. |
| 2014/0138558 A1 | 5/2014 | Damiano, Jr. et al. |
| 2018/0136148 A1* | 5/2018 | Zhang .................. G01N 23/22 |

FOREIGN PATENT DOCUMENTS

| | | |
|---|---|---|
| JP | H0227111 | 2/1990 |
| JP | 2013535795 | 9/2013 |
| TW | 200826141 | 6/2008 |
| TW | 201209401 | 3/2012 |

OTHER PUBLICATIONS

Yang et al., "In situ SEM and ToF-SIMS analysis of IgG conjugated gold nanoparticles at aqueous surfaces," Surf. Interface Anal., Mar. 2013, pp. 224-228.

"Office Action of Japan Counterpart Application," dated Aug. 29, 2017, p. 1-p. 4.

"Office Action of Taiwan Counterpart Application", dated Sep. 13, 2016, p. 1-p. 6.

"Office Action of China Counterpart Application", dated Jun. 26, 2018, p. 1-p. 6.

* cited by examiner

SAMPLE COLLECTION DEVICE AND MANUFACTURING METHOD THEREOF

CROSS-REFERENCE TO RELATED APPLICATION

This application claims the priority benefit of Taiwan application serial no. 105111188, filed on Apr. 11, 2016. The entirety of the above-mentioned patent application is hereby incorporated by reference herein and made a part of this specification.

BACKGROUND

Field of the Invention

The invention is directed to a sample collection device and more particularly, to a sample collection device that can be applied in an electron microscope.

Description of Related Art

With the advance in microscopy technology, various microscopic observation apparatuses, such as atomic force microscopes (AFM), electron microscopes (e.g., transmission electron microscopes (TEM) and scanning electron microscopes (SEM)), and so on, have been invented. Additionally, different types of sample collection devices, e.g., gaseous or liquid solution sample test pieces, dry sample test pieces and so on, are required for different microscopes.

In a known technique, a micro channel for a liquid solution sample can be formed in a sample collection device by combining a silicon chip and polydimethylsiloxane (PDM) commonly used for manufacturing a micro-electro mechanical system in an oxygen plasma bonding manner, for example. However, the aforementioned technique can only be applied to an energy-dispersive X-ray spectroscopy (EDX) in an SEM for observing and analyzing variation in a specific component and concentration of a surface area of a fluid sample in a lower resolution.

Additionally, U.S. Patent Publication No. US2013/0264476A1 discloses a sample collection device with a micro-channel formed by combining a silicon chip and a sample holder of a TEM. When a liquid fluid sample enters the micro-channel of the sample collection device, the actual distribution of particles in the liquid fluid sample can be observed by the TEM. However, the sample collection device can only be used in the TEM, but cannot be applied to other types of electron microscopes, such as the SEM, nor the observation of chemical reactions or electrochemical reactions. Besides, the sample collection device is also incapable of effectively controlling a flow mode of a liquid sample.

SUMMARY

The invention provides a sample collection device capable of being applied to various types of electron microscopes and effectively controlling flow directions and velocities of a liquid sample through structure changes of a containing space of the sample.

The invention provides a sample collection device capable of selectively disposing recesses in one of two oppositely disposed substrates according to observation demands for a sample, so as to form a sample containing space for containing a liquid solution sample and allow the liquid solution sample to flow in and out.

The invention provides a manufacturing method of a sample collection device for manufacturing a sample collection device having channels with difference sizes for a liquid sample and being capable of effectively controlling velocities and flow directions of the liquid sample.

According to an embodiment of the invention, a sample collection device including two substrates and a spacer is provided. The two substrates are disposed oppositely. Each substrate has a first surface, a second surface opposing to the first surface, a first recess and at least one second recess. The two substrates are disposed with the first surfaces facing each other, and the first and the at least one second recesses are respectively located in the first surfaces. The first recesses of the substrates jointly form a first channel, and the second recesses of the substrates jointly form at least one second channel connected to the outside of the sample collection device. The first channel and the at least one second channel are interconnected. The spacer is disposed between the two first surfaces to bond and fix the two substrates. A sample containing space is formed between the two substrates and the spacer. The sample containing space includes the first channel and the at least one second channel.

According to an embodiment of the invention, a sample collection device including two substrates and a spacer is provided. The two substrates are disposed oppositely. Each of the substrates includes a first surface and a second surface opposite to the first surface. One of the two substrates has a first recess and at least one second recess, the first and second recesses are respectively located in the first surface, and the second recess is connected to the outside of the sample collection device. The two substrates are disposed with the two first surfaces facing to each other, and the first recess and the second recesses are interconnected. The spacer is disposed between the two first surfaces to bond and fix the two substrates. A sample containing space is surrounded by and formed between the two substrates and the spacer.

According to an embodiment of the invention, a manufacturing method of a sample collection device is provided, which includes the following steps. A first recess and at least one second recess are formed on a first surface of a semiconductor substrate. An insulating layer is formed on the first surface and a second surface opposite to the first surface of the semiconductor substrate. The insulation layer located on the first surface and the second surface is patterned, and a partial area of the second surface is exposed by the insulation layer on the second surface. The steps are repeatedly performed on another substrate. The two semiconductor substrates are bonded to each other through the insulation layer on the two first surfaces. A spacer is formed by the insulation layer on the two first surface to bond and fix the two semiconductor substrates. A first channel is jointly formed by the two first recesses, and at least one second channel is jointly formed by the two second recesses. The first channel and the second channel are interconnected. A sample containing space is formed between the two substrates and the spacer. The sample containing space includes the first chancel and the second channel.

In an embodiment of the invention, the first channel and the at least one second channel respectively have a first depth and a second depth, and the second depth is greater than the depth.

In an embodiment of the invention, the first depth ranges from 0.01 μm to 10 μm.

In an embodiment of the invention, the second depth ranges from 0.1 μm to 400 μm.

In an embodiment of the invention, each of the substrates further includes an observation window, the observation window is disposed on the second surface and corresponding to the first channel of the sample containing space.

In an embodiment of the invention, the sample collection device further includes an inlet and an outlet. The inlet is located in an opening at one end of one of the first channel and the at least one second channel, and the outlet is located in an opening at the other end of one of the first channel and the at least one second channel.

In an embodiment of the invention, the sample collection device further includes an inlet and an outlet. The inlet is located in an opening at one end of the at least one second channel, and the outlet is located in an opening the other end of the at least one second channel.

In an embodiment of the invention, the number of the at least one second channel is two, and a longitudinal extension direction of the second channels is parallel to a longitudinal extension direction of the first channel.

In an embodiment of the invention, two ends of each of the second channels respectively have an inlet and an outlet, and the inlet of one of the second channels and the outlet of the other second channel are located at the same side.

In an embodiment of the invention, one of the substrates has an inlet located on the second surface of the substrate, and the inlet is connected with one of the second channels. The other substrate has an outlet located on the second surface of the substrate, and the outlet is connected with the other second channel.

In an embodiment of the invention, one of the substrates has an inlet and an outlet, and the inlet and the outlet are respectively located on the second surface of the substrate and respectively connected with at least one of the second channels.

In an embodiment of the invention, the sample collection device further includes at least one set of reaction electrodes disposed in the first channel.

In an embodiment of the invention, the sample collection device further includes at least one set of heating elements or sensing elements disposed in the at least one second channel.

In an embodiment of the invention, the sample collection device further includes at least one set of heating elements or sensing elements disposed near an opening at one end of the at least one second channel.

In an embodiment of the invention, at least one of the two substrates has an observation window disposed on the second surface and corresponding to the first recess.

In an embodiment of the invention, the manufacturing method of the sample collection device further includes forming an observation window in the partial area of the second surface of each of the semiconductor substrates which is exposed by the insulation layer. The observation window penetrates the semiconductor substrate and exposes part of the insulation layer located on the first surface.

In an embodiment of the invention, the manufacturing method of the sample collection device further includes forming an inlet or an outlet on the first surface or the second surface of each of the semiconductor substrates, and the inlet or the outlet is connected with the at least one second channel.

In an embodiment of the invention, the manufacturing method of the sample collection device further includes forming a heating or sensing element on a surface of the at least one second recess of the semiconductor substrate.

In an embodiment of the invention, the manufacturing method of the sample collection device further includes forming a heating or sensing element near an opening of one end of the at least one second recess of the semiconductor substrate.

In an embodiment of the invention, the manufacturing method of the sample collection device further includes forming a metal wire on the heating or sensing element.

In an embodiment of the invention, a method of forming the metal wire includes metal sputtering or lift-off.

In an embodiment of the invention, a method of bonding the insulation layer on the first surfaces of the two semiconductor substrates includes anodic bonding or high-temperature fusion bonding.

In an embodiment of the invention, a method of forming the first recess and the at least one second recess includes etching the semiconductor substrate by using the insulation layer on the first surface or coating a photoresist and defining a pattern on the insulation layer as a mask.

In an embodiment of the invention, a method of etching the semiconductor substrate includes dry etching.

To sum up, the sample containing space of the sample collection device of the invention includes the first chancel and the second channel. The first channel and the second channels are located between the two substrates and the spacer, and the first channel and the second channel are interconnected. Thereby, the sample collection device can achieve affecting and controlling the flow directions and states of the liquid solution sample in the first channel through changing the flow manners and directions of the liquid solution sample in the second channel. In addition, the sample collection device of the invention can be applied to various types of electron microscopes, and the electron microscope can obtain the distribution of particles in the liquid solution sample by observing the flow state of the liquid solution sample in the first channel of the sample collection device.

To make the above features and advantages of the invention more comprehensible, embodiments accompanied with drawings are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1A:
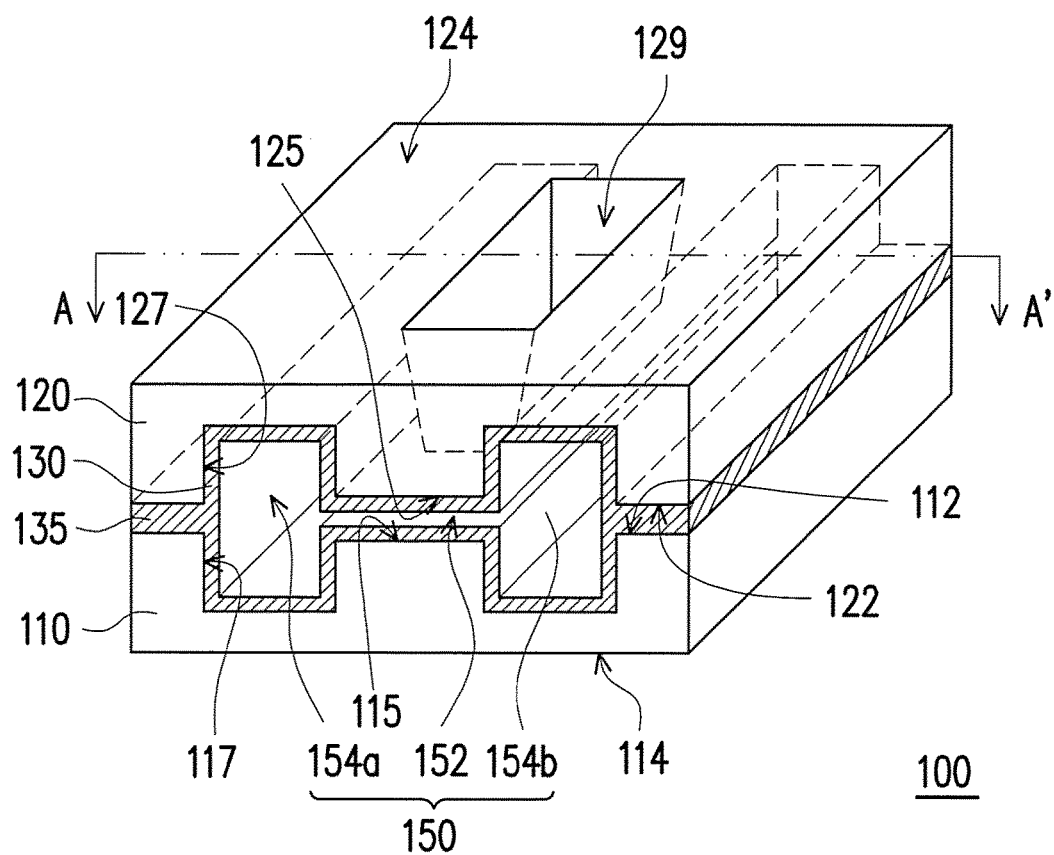
FIG. 1A is a schematic three-dimensional diagram illustrating a sample collection device according to an embodiment of the invention.

In the embodiments provided below, the same or similar symbols represent components or devices having the same or similar functions, wherein shapes, sizes and ratios of the devices in the drawings are merely schematically illustrated and construe no limitations to the invention. Additionally, although several technical features may be simultaneously described in any one of the embodiments below, it does not indicate that all the technical features have to be simultaneously implemented in the embodiment.

Figure 1B:
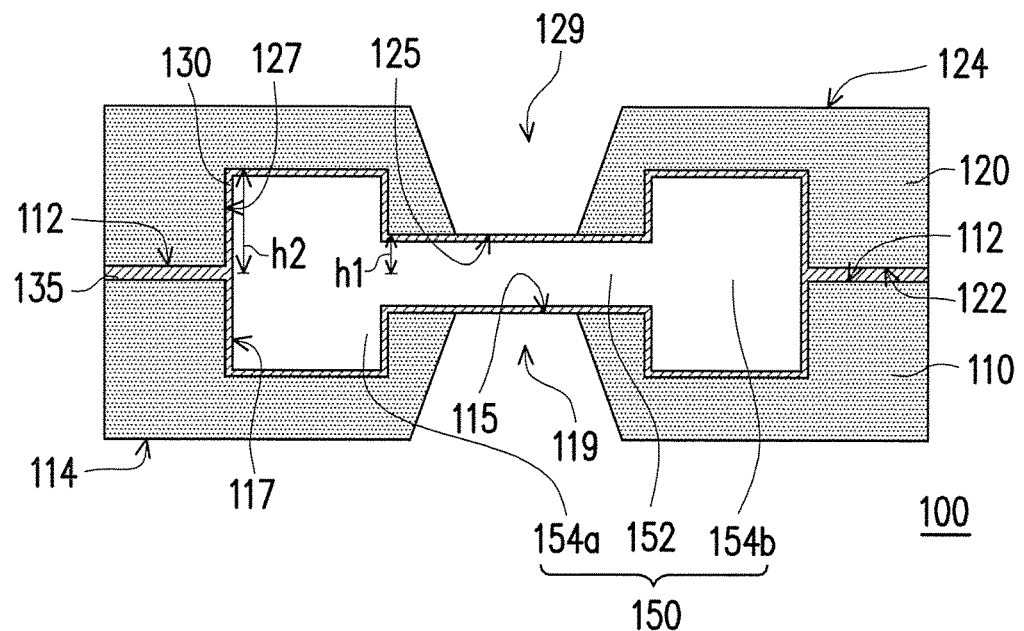
FIG. 1B is a cross-sectional diagram illustrating the sample collection device depicted in FIG. 1A along line A-A'.
Figure 1C:
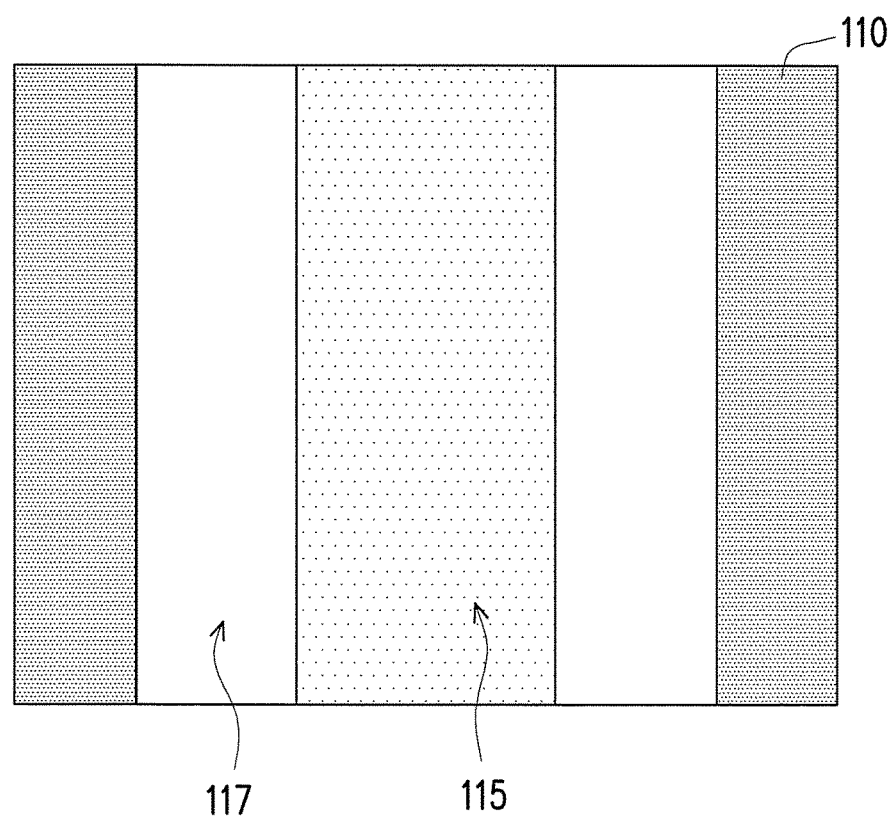
FIG. 1C is a schematic top-view diagram illustrating the substrate depicted in FIG. 1A.

FIG. 1A is a schematic three-dimensional diagram illustrating a sample collection device according to an embodiment of the invention. FIG. 1B is a cross-sectional diagram illustrating the sample collection device depicted in FIG. 1A along line A-A'. FIG. 1C is a schematic top-view diagram illustrating the substrate 110 depicted in FIG. 1A. Referring to FIG. 1A, FIG. 1B, and FIG. 1C, a sample collection device 100 of the present embodiment includes substrates 110 and 120 and a spacer 135. The two substrates 110 and 120 are disposed oppositely, for example, stacked vertically. The substrate 110 has a first surface 112 and a second surface 114 which are opposite to each other, and the substrate 120 has a first surface 122 and a second surface 124 which are opposite to each other. The substrate 110 and the substrate 120 are disposed with the first surface 112 and the first surface 122 facing each other. Referring to FIG. 1B, the substrate 110 has a first recess 115 and at least one second recess 117 (illustrated as two in FIG. 1B, for example), and the first recess 115 and the second recesses 117 are respectively located in the first surface 112 of the substrate 110. In the same way, the substrate 120 has a first recess 125 and at least one second recess 127, and the first recess 125 and the second recesses 127 are respectively located in the first surface 122 of the substrate 120. In the present embodiment, the first recess 115 of the substrate 110 and the first recess 125 of the substrate 120 jointly form a first channel 152, and the second recesses 117 of the substrate 110 and the second recesses 127 of the substrate 120 jointly form second channels 154a and 154b (illustrated as two channels in FIG. 1B, for example). In addition, referring to FIG. 1A and FIG. 1B, the first channel 152 and the second channels 154a and 154b are interconnected.

In the present embodiment, the spacer 135 is disposed between the first surface 112 of the substrate 110 and the first surface 122 of the substrate 120, so as to bond and fix the substrates 110 and 120. A sample containing space 150 is formed between the substrates 110 and 120 and the spacer 135, and the sample containing space 150 includes the interconnected first channel 152 and second channels 154a and 154b. In the present embodiment, the sample containing space 150 defined by the substrate 110, the substrate 120 and the spacer 135 is, for example, a flow path with openings at a front end and a rear end. A liquid solution sample may flow in the sample containing space 150 from one of the ends and flow out of the sample containing space 150 through the other end. A transmission electron microscope (TEM) or a scanning electronic microscope (SEM) may be used for quantitatively observing types, shape distributions, size distributions, aggregation/agglomeration states and concentrations of particles in the liquid solution sample during the process of the liquid solution sample flowing through the sample containing space 150. For example, the particles may be nano-medicines in the blood, while the liquid solution sample may be from the human blood.

In the present embodiment, an insulation layer 130 may be disposed on the first surface 112 of the substrate 110 and the first surface 122 of the substrate 120. In the present embodiment, the insulation layer 130 on the bonding part between the first surface 112 of the substrate 110 and the first surface 122 of the substrate 120 may serve as the spacer 135 between the substrate 110 and the substrate 120 after being bonded. In addition, the insulation layer 130 may serve as a protection layer or a mask layer for part of a surfaces of each of the substrates 110 and 120 in an etching process of the sample collection device. In the present embodiment, a material for forming the insulation layer 130 is, for example, a silicon nitride film. In addition, the material of the insulation layer 130 may also be silicon oxide or a composite film jointly composed of silicon nitride and silicon oxide.

Referring to FIG. 1B again, in the present embodiment, the substrates 110 and 120 further include observation windows 119 and 129, respectively, and the observation windows 119 and 129 are respectively disposed on the second surface 114 of the substrate 110 and the second surface 124 of the substrate 120. The observation windows 119 and 129 are respectively corresponding to the first channel 152 of the sample containing space 150 and expose the insulation layer 130 on part of the first surfaces 112 and 122. In the present embodiment, a flow state of the liquid solution sample in the sample containing space 150 may be observed by the TEM through the observation windows 119 and 129.

Referring to FIG. 1B, the first recess 115 of the substrate 110 and the first recess 125 of the substrate 120 respectively have a depth h1 in a direction perpendicular to the first surfaces 112 and 122, which refers to a distance from each of the first surfaces 112 and 122 to the bottom of each of the first recesses 115 and 125. The second recess 117 of the substrate 110 and the second recess 127 of the substrate 120 respectively have a depth h2 in a direction perpendicular to the first surfaces 112 and 122, which refers to a distance from the first surfaces 112 and 122 to the bottom of each of the second recesses 117 and 127. The second depth h2 is greater than the depth h1. A height of the first channel 152 jointly formed by the first recesses 115 and 125 is twice the first depth h1, and a height of each second channel 154 jointly formed by the second recesses 117 and 127 is twice the second depth h2. Thus, the height of the second channel 154 in the perpendicular direction is greater than the height of the first channel 152, and a sectional area of the second channel 154 is greater than that of the first channel 152 in the cross-sectional diagram illustrated in FIG. 1B. When the liquid solution sample flows through the first channel 152 and the second channel 154 in the sample containing space 150, due to the first channel 152 and the second channel 154 having different sizes of sectional areas, a pressure drop required by the liquid solution sample during the process of flowing may be dramatically reduced by the second channel 154 having the greater sectional area, and different types of flow field structures may be formed in the first channel 152 having the smaller sectional area.

FIG. 2A to FIG. 2D are schematic diagrams illustrating flow field structures in the sample containing space of the sample collection device depicted in FIG. 1A. In FIG. 2A to FIG. 2D, the black solid arrows are used to indicate a flow direction of the liquid solution sample in the first channel 152, the white solid arrows are used to indicate flow directions of the liquid solution sample in the second channels 154a and 154b, and a size of a dashed-line range in the first channel 152 represents relative variation of flow velocities of the liquid solution sample. To be detailed, referring to FIG. 2A, when the flow velocities of the liquid solution sample in the two second channels 154a and 154b of the sample containing space 150 are equal, the liquid solution sample may evenly move forward in an equal flow velocity in the first channel 152. In addition, referring to FIG. 2B, when the flow velocity of the liquid solution sample in one of the two second channels 154a and 154b is greater than that in the other second channel, the flow velocity of the liquid solution sample flowing through the first channel 152 is affected by unevenness of the flow velocities of the liquid solution sample in the two second channels 154, such that the flow velocity of the liquid solution sample in the first channel 152 is decreased from one side close to the second channel 154b having the faster flow velocity toward the other side close to the second channel 154a having the slower flow velocity, which causes a gradient change to the flow velocity of the liquid solution sample in the first channel 152.

Figure 2A:
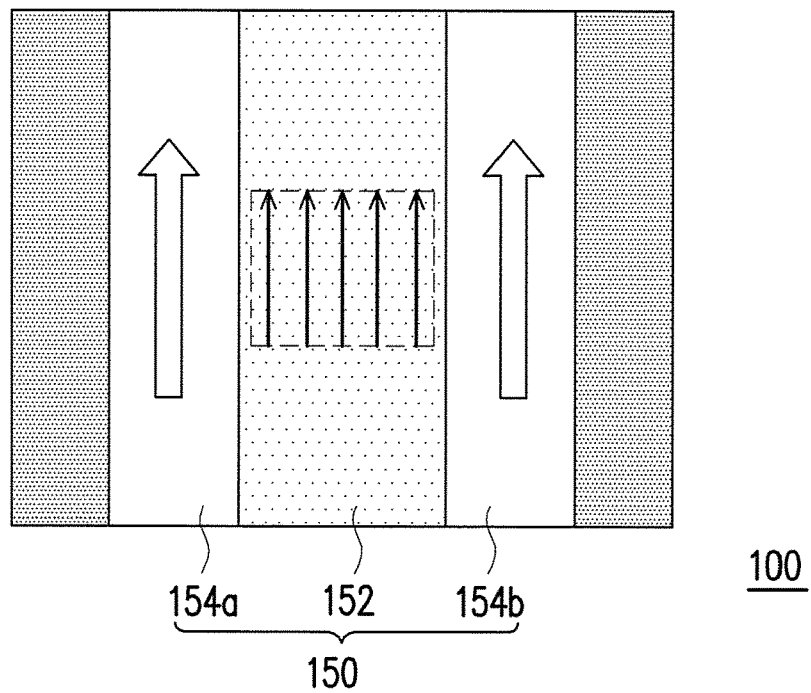
FIG. 2A to FIG. 2D are schematic diagrams illustrating flow field structures in the sample containing space of the sample collection device depicted in FIG. 1A.
Figure 2B:
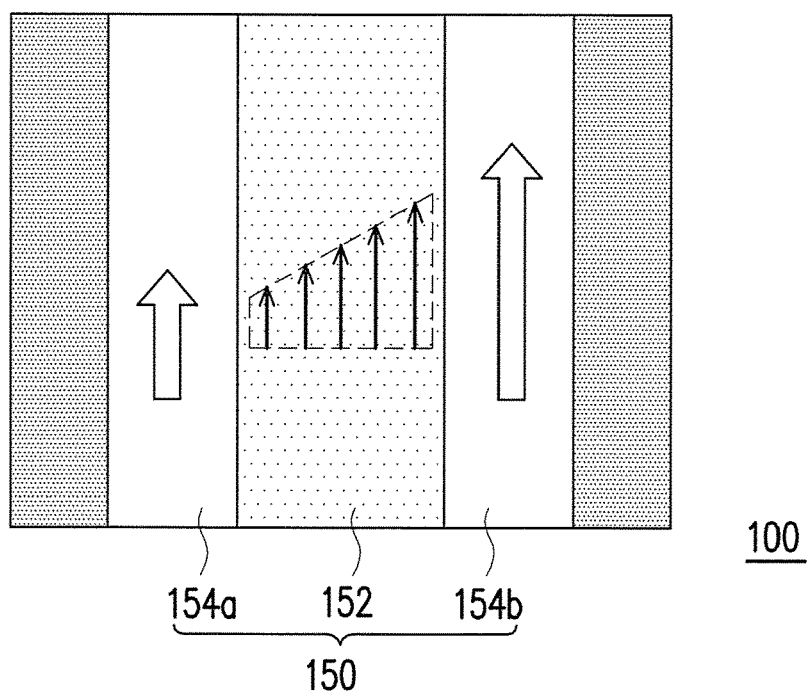
Figure 2C:
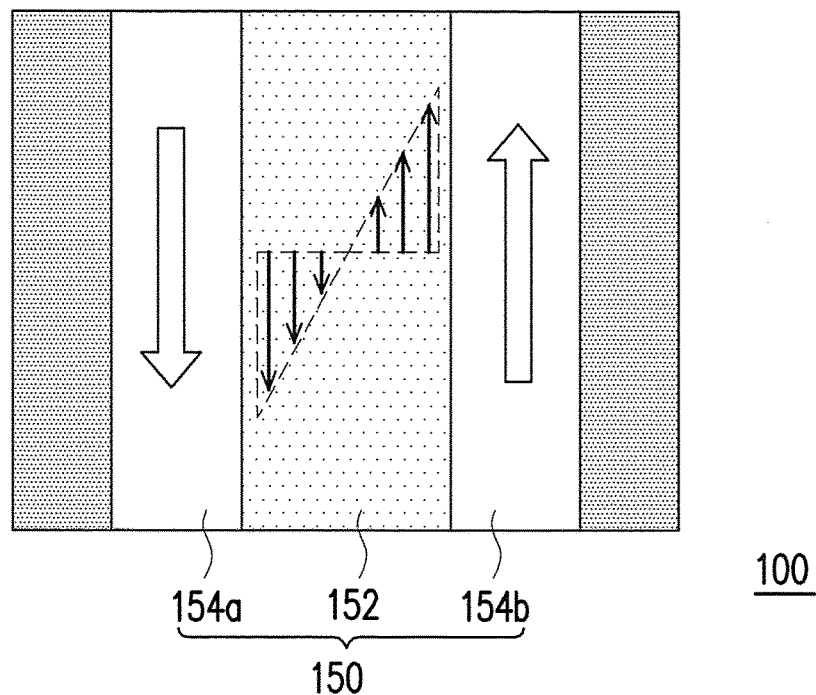

Referring to FIG. 2C, when the liquid solution sample flows in opposite directions in the second channels 154a and 154b, the flow direction of the liquid solution sample in the first channel 152 has an opposite distribution as the liquid solution sample has different flow directions in the second channels 154a and 154b. That is to say, the liquid solution sample at the side in the first channel 152 which is close to the second channel 154a flows in the same direction as that in the second channel 154a, and the liquid solution sample at the other side which is close to second channel 154b flows in the same direction as that in the second channel 154b due to being respectively driven by the liquid solution sample in the second channels 154a and 154b. Thus, the liquid solution sample in the first channel 152 is separated in opposite directions. In addition, referring to FIG. 2C, after the liquid solution sample in the first channel 152 is separated in opposite directions from the middle of the first channel 152, the flow velocity is linearly increased toward the second channels 154a and 154b at the two sides.

Figure 2D:
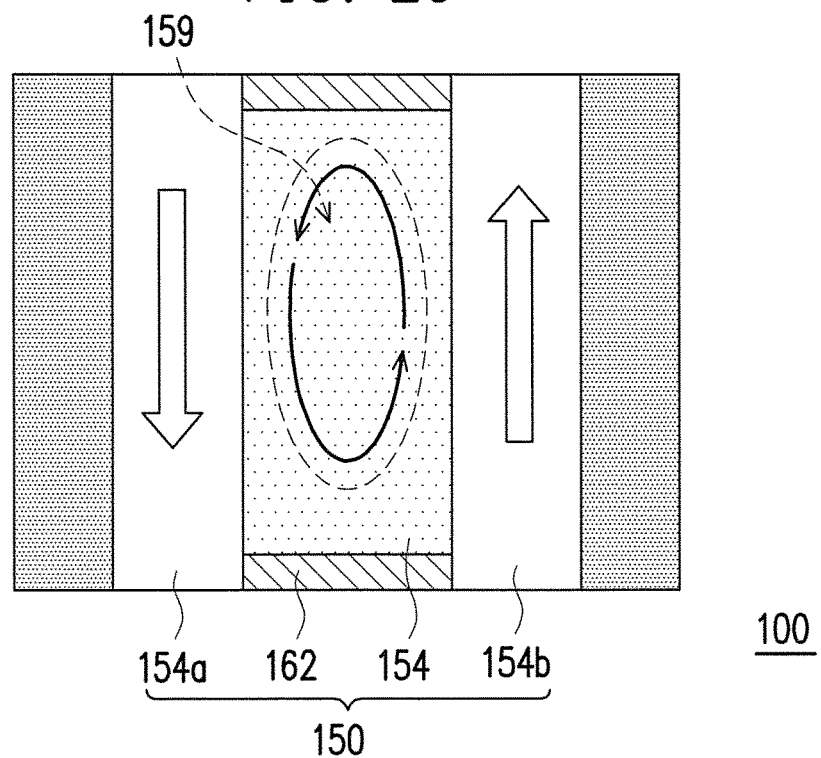

Referring to FIG. 2D, when the liquid solution sample flows in opposite directions in the second channels 154a and 154b, such that the liquid solution sample flowing through the first channel 152 is separated in opposite directions, the liquid solution sample in the second channels 154a and 154b flows in the first channel 152 in opposite directions if a blocking zone 162 is disposed at each of the two ends of the first channel 152 to stop the liquid solution sample from flowing in or flowing out of the first channel 152, such that a recirculation zone 159 is formed in the first channel 152, which causes a stirring effect to the liquid solution sample itself.

In the present embodiment, when the flow velocity of the liquid solution sample in the first channel 152 of the sample containing space 150 encounters the gradient change, the distribution of the particles of the liquid solution sample in different flow velocities may be observed by the TEM.

Figure 3A:
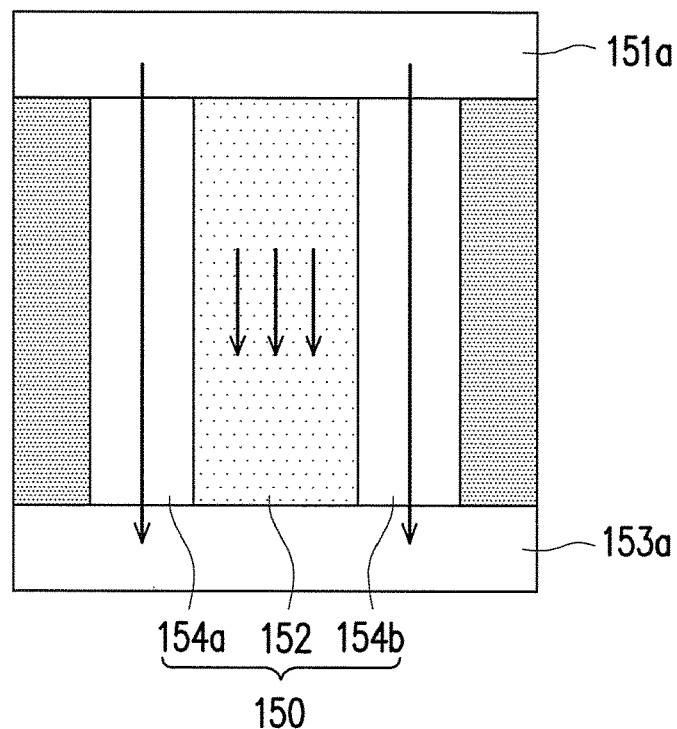
FIG. 3A to FIG. 3C are schematic diagrams illustrating a sample collection device according to another embodiment of the invention.
Figure 3B:
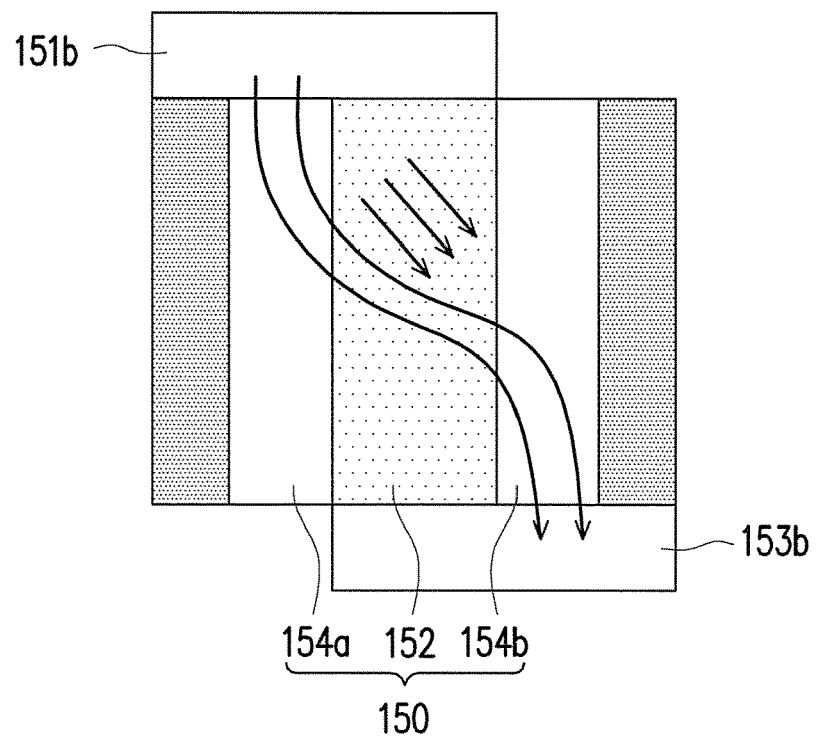
Figure 3C:
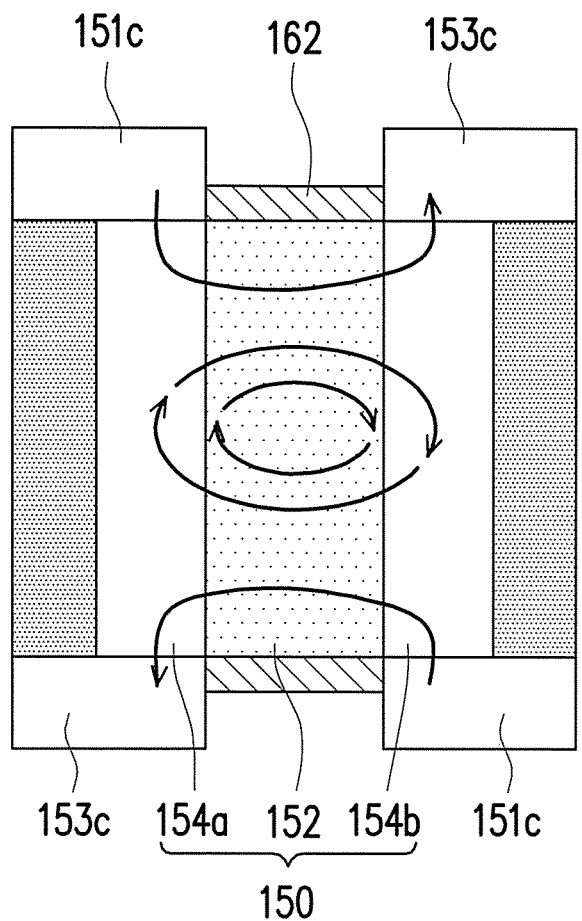

FIG. 3A to FIG. 3C are schematic diagrams illustrating a sample collection device according to another embodiment of the invention. In FIG. 3A to FIG. 3C, the black solid arrows are used to indicate the flow directions of the liquid solution sample in the sample containing space 150. In the present embodiment, at least one common inlet and at least one common outlet of the liquid solution sample may be respectively disposed in openings at two ends of the first channel 152 and openings at two ends of at least one of the second channels 154a and 154b. For example, referring to FIG. 3A, a single inlet 151a connected with one end of each of the first channel 152 and the second channels 154a and 154b may be formed outside the sample containing space 150, such that the liquid solution sample may simultaneously flow in the first channel 152 and the two second channels 154a and 154b through the inlet 151a. In addition, a single outlet 153a may also be formed the other end of each of the first channel 152 and the second channels 154a and 154b of the sample containing space 150, such that the liquid solution sample may simultaneously flow out of the first channel 152 and the two second channels 154a and 154b through the outlet 153a. In the present embodiment, the disposition of the inlet 151a and the outlet 153a facilitates the liquid solution sample in flowing in and out of the sample containing space 150 evenly in the same direction.

Referring to FIG. 3B, an inlet 151b of the sample containing space 150 may also be only connected with the openings of one end of the first channel 152 and one of the second channels 154a and 154b, an outlet 153b of the sample containing space 150 may also be only connected with the openings of the other end of the first channel 152 and the other one of the second channels 154a and 154b. The biased disposition manner of the inlet 151a and the outlet 153b causes the liquid solution sample flowing in the sample containing space 150 to flow bias among the first channel 152 and the two second channels 154a and 154b, as illustrated in FIG. 3B.

Referring to FIG. 3C, in the present embodiment, the blocking zones 162 may be disposed in the openings at the two ends of the first channel 152, and an inlet 151c and an outlet 153c may be respectively disposed in the openings of the second channels 154a and 154b at the same side, such that the liquid solution sample may flow in and out in single way along the arrow direction illustrated in FIG. 3C through the openings of the second channels 154a and 154b at the same side. In addition, the opening at the other end of the second channel 154a may be disposed with an outlet 153c for the liquid solution sample, while the opening at the other end of the second channel 154b may be disposed with an inlet 151c for the liquid solution sample. Thereby, a channel in single way may also be formed along the arrow direction illustrated in FIG. 3C between the openings of the second channels 154a and 154b at the other side. Thus, the liquid solution sample may also flow in and out of the sample containing space 150 through the inlet 151c and the outlet 153c in the openings of the second channels 154a and 154b at the other side. In addition, when the blocking zones 162 are disposed in the openings at the two ends of the first channel 152, the liquid solution sample flows in and out in single way along opposite directions through the openings of the second channels 154a and 154b at each side, such that a recirculation flow is formed in the first channel 152, which causes a stirring effect to the liquid solution sample.

In the above embodiment, the sample collection device 100 may achieve changing the flow manner and the flow directions of the liquid solution sample in the sample containing space 150 by changing the disposition manner of the inlets and the outlets of the sample containing space 150 and thus, is adapted for observing the distribution of the particles in the liquid solution sample of different types.

Figure 4A:
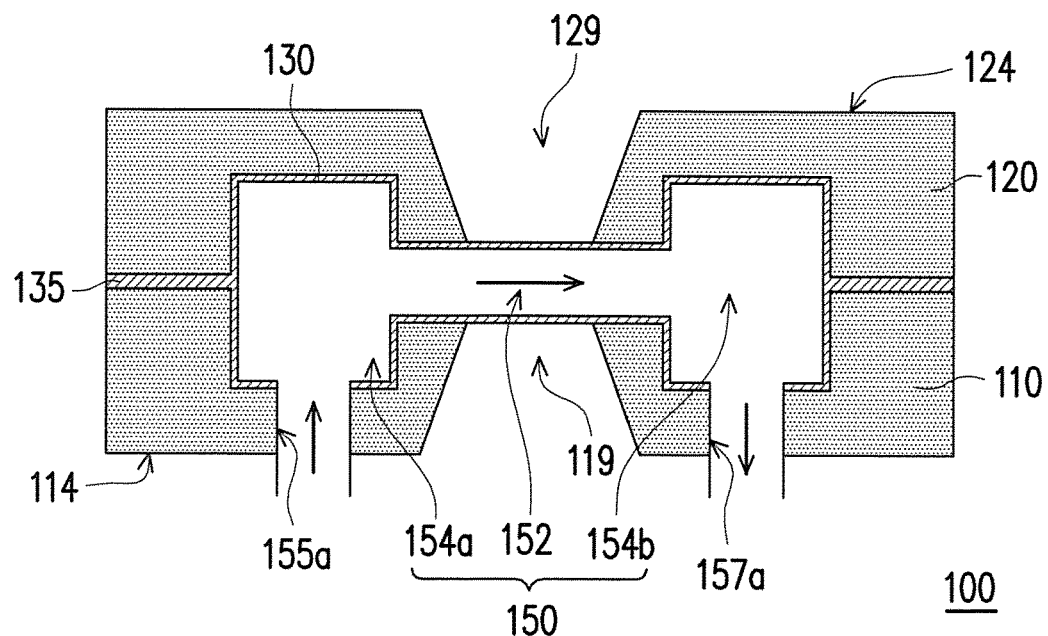
FIG. 4A to FIG. 4C are schematic diagrams illustrating a sample collection device according to another embodiment of the invention.
Figure 4B:
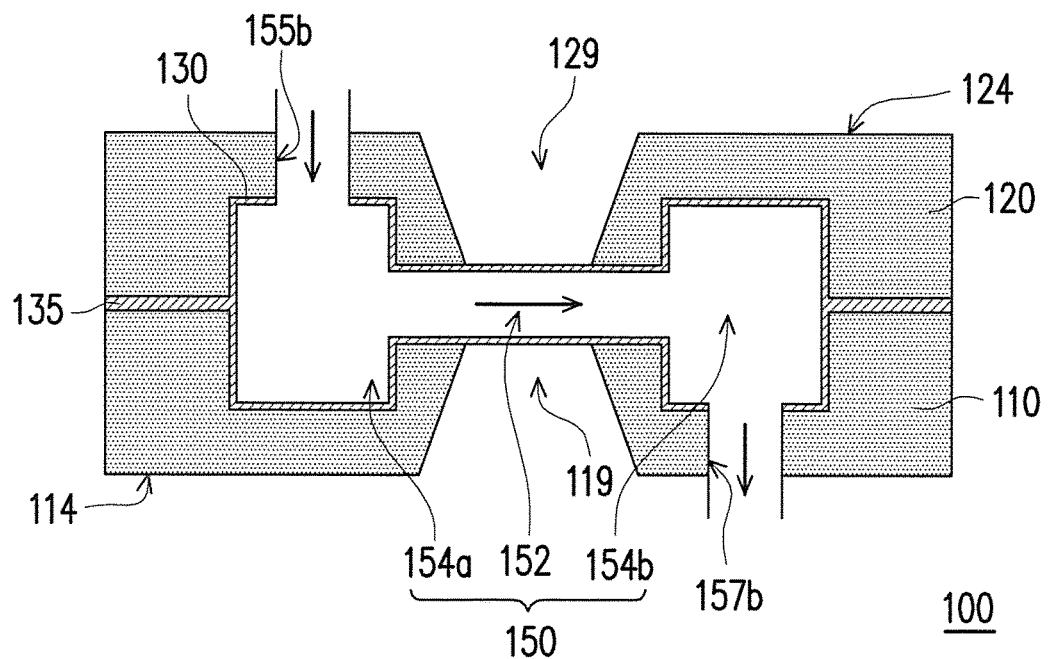
Figure 4C:
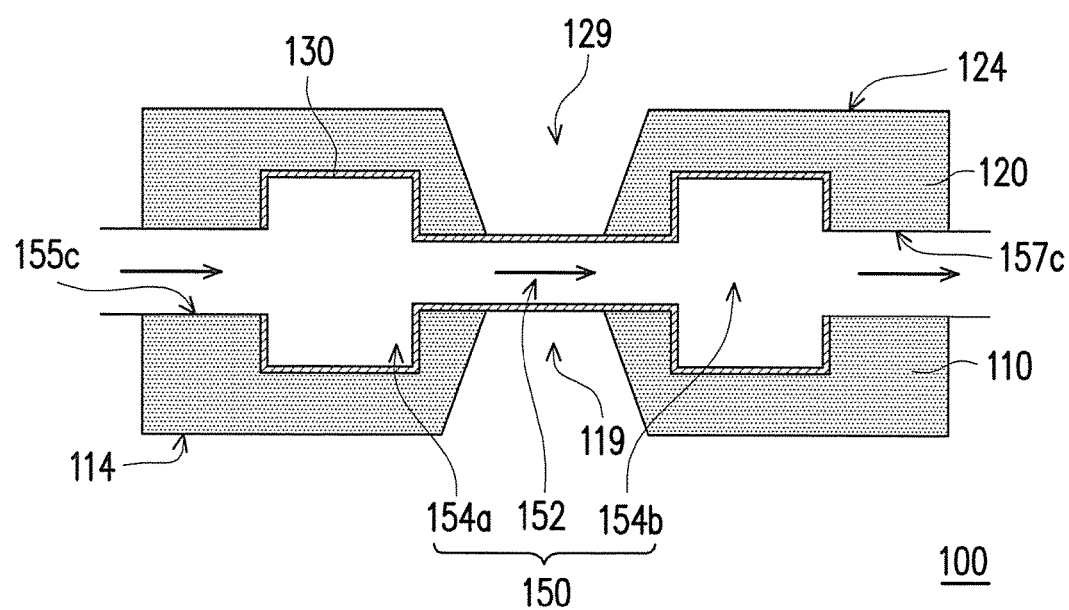

FIG. 4A to FIG. 4C are schematic diagrams illustrating a sample collection device according to another embodiment of the invention. In FIG. 4A to FIG. 4C, the black solid arrows are used to indicate the flow direction of the liquid solution sample. Referring to FIG. 4A, in the present embodiment, an inlet 155a and an outlet 157a of the sample collection device 100 are disposed on the second surface 114 of the substrate 110 of the sample collection device 100 and correspondingly connected with the second channels 154a and 154b respectively. Thus, the liquid solution sample may flow in the sample containing space 150 from one side of the second surface of the sample collection device 100.

Referring to FIG. 4B, in the present embodiment, an inlet 155b of the sample collection device 100 for the liquid solution sample is disposed on the second surface 124 of the substrate 120 and corresponding to the second channel 154a, while an outlet 157b is disposed on the second surface 114 of the substrate 110 and corresponding to the second channel 154b. Thereby, referring to FIG. 4B, the inlet 155a and the outlet 157a for the liquid solution sample are respectively disposed on the upper and the lower sides of the sample collection device 100. Thus, the liquid solution sample may flow in the sample collection device 150 from the inlet 155a on the upper side and flow out of the sample collection device 100 through the outlet 157b on the lower side.

Referring to FIG. 4C, in the present embodiment, an inlet 155c and outlet 157c of the sample collection device 100 may also be disposed at intersections of the substrates 110 and 120 which are perpendicular to sides of the second surfaces 114 and 124, such that the inlet 155c is corresponding to the second channel 154a, and the inlet 157c is corresponding to the second channel 154b. Thus, the liquid solution sample may flow in and out of the sample containing space 150 through the inlet 155c and the 157c disposed at the two sides of the sample collection device 100, such that a lateral flow path is generated in a direction perpendicular to a longitudinal extension direction of the first channel 152 and a longitudinal extension direction of the second channels 154a and 154b.

In the present embodiment, the sample collection device 100 may achieve changing the flow directions and positions of flowing in and out of the sample containing space 150 for the liquid solution sample through changing the disposition manner and the positions of the inlets and the outlets of the sample containing space 150 and thereby, is adapted to various demands for sample observation.

Figure 5A:
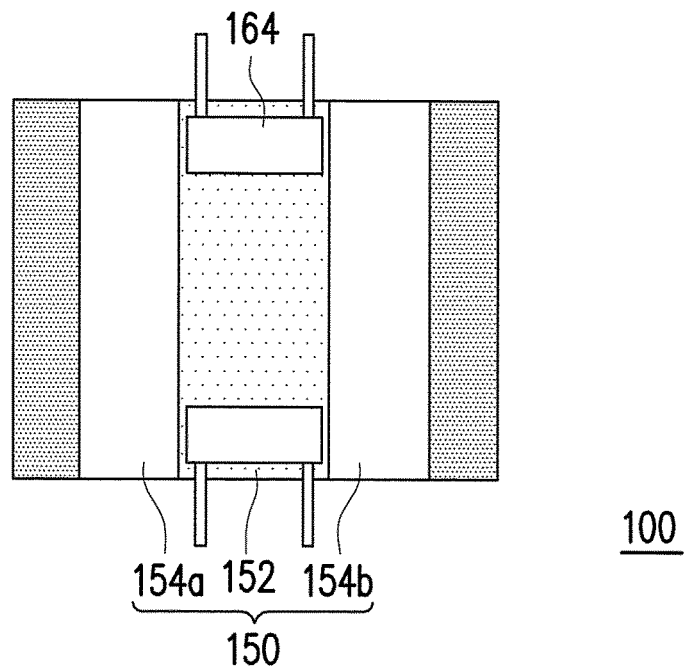
FIG. 5A to FIG. 5C are schematic diagrams illustrating a sample collection device according to another embodiment of the invention.
Figure 5B:
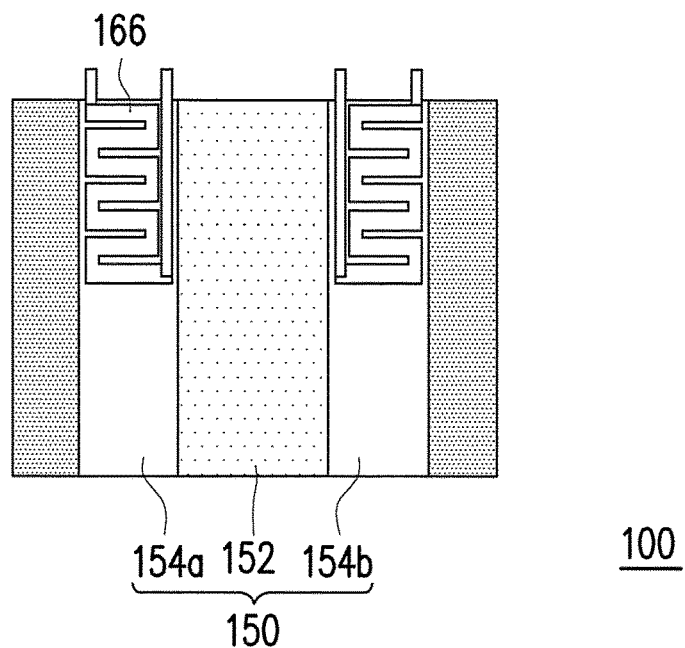
Figure 5C:
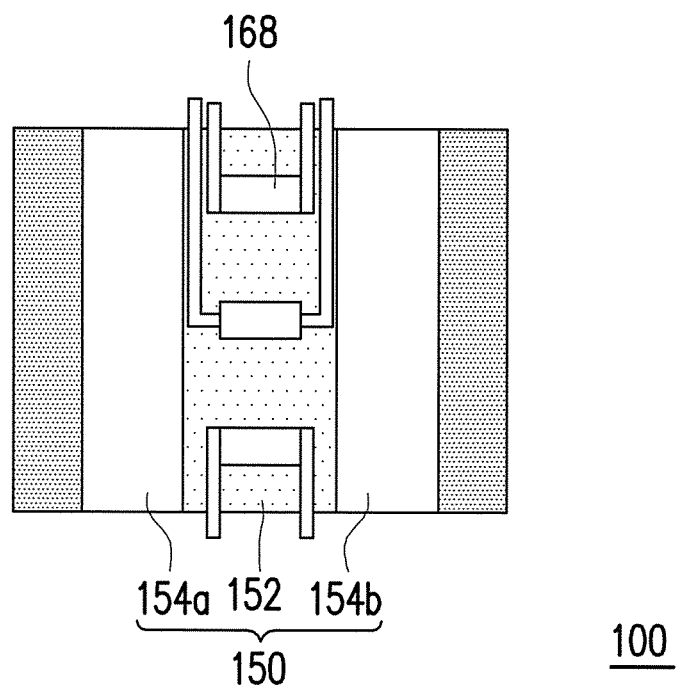

FIG. 5A to FIG. 5C are schematic diagrams illustrating a sample collection device according to another embodiment of the invention. Referring to FIG. 5A, in the present embodiment, a reaction electrode 164 including an anode and a cathode may be disposed on the first channel 152 of the sample containing space 150. As being affected by an electric field of the reaction electrode 164, different particles in the liquid solution sample flowing through the reaction electrode 164 have different moving velocities in the electric field, so as to achieve an electrophoretic separation effect. Thereby, a composition and a concentration of a compound solution may be further analyzed by the sample collection device 100 through the disposition of the reaction electrode 164. In the present embodiment, the reaction electrode 164 may be made of platinum (Pt), copper (Cu), titanium (Ti), chromium (Cr), wolfram (W) or a combination of the aforementioned metal materials. In addition, the reaction electrode may also be made of a semiconductor material, such as polysilicon, aluminum nitride (AlN), aluminum oxide (AlO2), zinc oxide (ZnO), titanium dioxide (TiO2) or a combination of the aforementioned materials.

Referring to FIG. 5B, heating elements 166 may be disposed in the second channels 154a and 154b of the sample containing space 150 to heat the liquid solution sample flowing through the second channels 154a and 154b, such that a temperature gradient is generated due to the liquid solution sample flowing through the inner side and the outer side of the first channel 152 being affected by the heating elements 166 in the second channels 154a and 154b. In the present embodiment, the heating elements 166 may be resistive filaments, which are made of a material, such as Cr or Ti. To be detailed, when the liquid solution sample in the second channels 154a and 154b is heated by the heating elements 166, the liquid solution sample flowing through the first channel 152 and at the two sides close to the second channels 154a and 154b has a higher temperature in comparison with liquid solution sample in the center inside the first channel 152. Thereby, the temperature of the liquid solution sample in the first channel 152 is gradually decreased from the two sides toward the middle of the first channel 152 to generate a temperature gradient. Therefore, the sample collection device 100 of the present embodiment may be applied to observe the distribution of the particles of a sample fluid in different temperature conditions or situations of composition and concentration changes for researches on object characteristics of samples.

Referring to FIG. 5C, in the present embodiment, a plurality of sensing elements 168 may also be disposed in the first channel 152, and the sensing elements 168 may sense a temperature or other physical properties of the liquid solution sample flowing through the first channel 152. For example, the sensing elements 168 may be platinum temperature sensors capable of sensing the temperature of the liquid solution sample flowing through the first channel 152. In the present embodiment, the sensing elements 168 may be respectively disposed at positions close to the openings at the two ends and in the center of the first channel 152, so as to sense temperature change before and after the liquid solution sample flows through the first channel 152. In addition, although the platinum temperature sensors are illustrated for example above, in other embodiments, the sensing elements 168 may also be made of any other metal material, e.g., Pt, Al, Cu, Ti and Cr. In addition, the sensing elements 168 may be made of a semiconductor material, e.g., polysilicon.

In the present embodiment, the reaction electrodes 164, the heating elements 166 and the sensing elements 168 described above may be collocated, combined and disposed in the first channel 152 and the sensing elements 154a and 154b, so as to be applied to studies and observations in regard to chemical reactions and electrochemical reactions of samples, such as cell reactions or electroplating mechanisms and others, e.g., the laminar flow technique and particle electrophoresis behaviors.

In another embodiment that is not shown, the heating elements 166 and the sensing elements 168 may also be disposed near the openings at the two ends of the second channels 154a and 154b. The disposition positions of the heating elements 166 and the sensing elements 168 may be adaptively adjusted according to various actual applications and sample observation demands, and the disposition manners and positions of the heating elements 166 and the sensing elements 168 are not particularly limited in the invention.

Figure 6A:
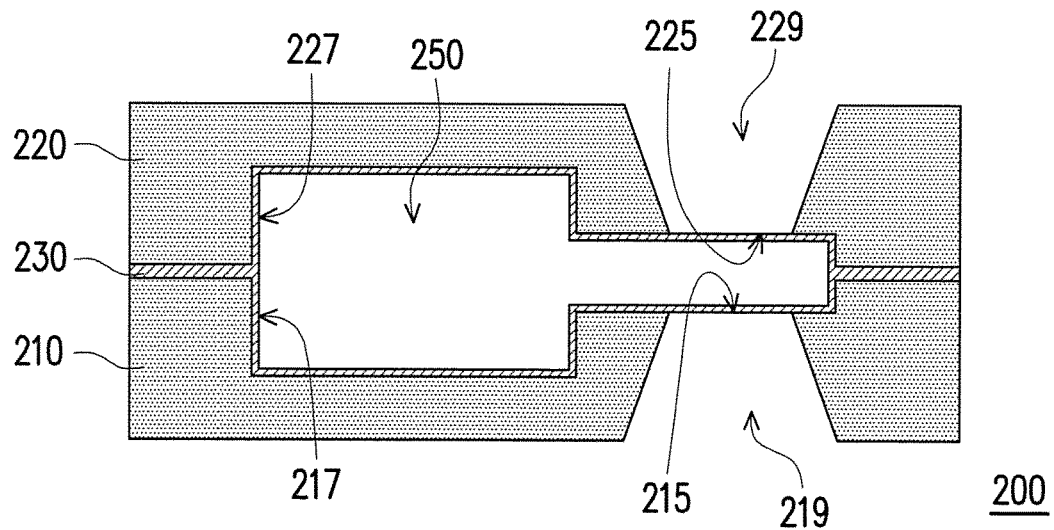
FIG. 6A to FIG. 6B are schematic diagrams illustrating a sample collection device according to another embodiment of the invention.
Figure 6B:
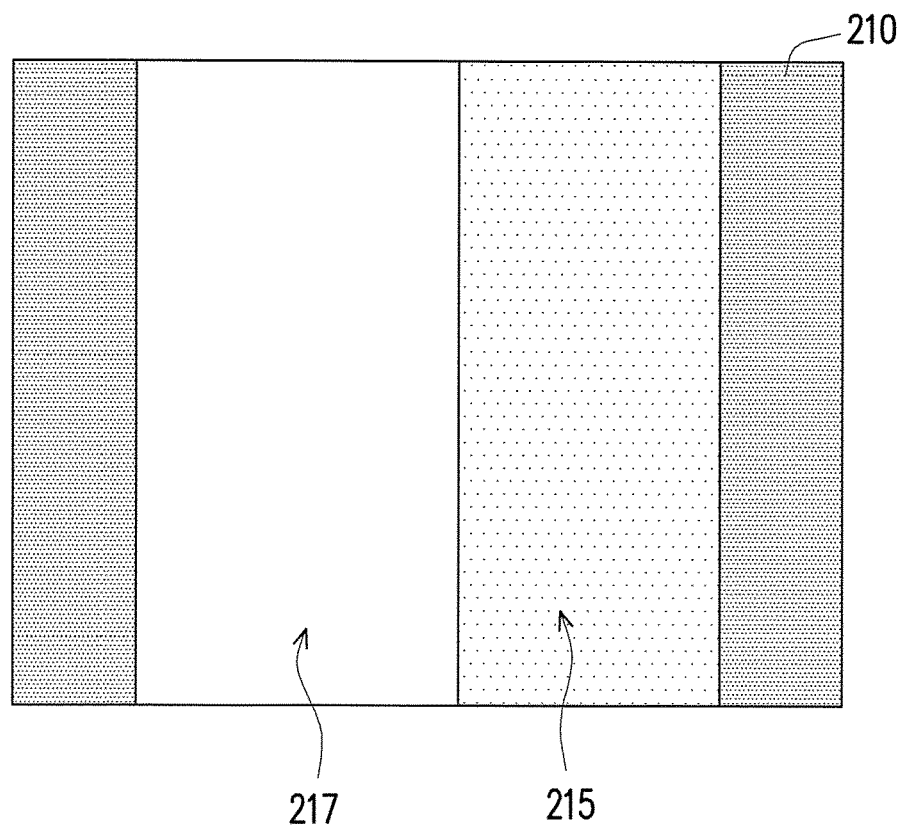

FIG. 6A to FIG. 6B are schematic diagrams illustrating a sample collection device according to another embodiment of the invention. In the present embodiment, a sample collection device 200 is different from the sample collection device in that only a second recess 217 is disposed on the substrate 210, and only a second recess 227 is disposed on the substrate 220 besides first recesses 215 and 225 respectively disposed in substrates 215 and 225 and an insulation layer 230 disposed thereon. In other words, in the sample collection device 200 of the present embodiment, the second recesses 217 and 227 are disposed one side of the first recess 215 and one side of the first recess 225. Thereby, the affection caused to the flow velocity and the flow direction of the liquid solution sample in a sample containing space 250 by the aforementioned element disposition may be observed by the TEM through observation windows 219 and 229. In the invention, the disposition manner, the positions and the numbers of the first recesses 215 and 225 and the second recesses 217 and 227 of the substrates 210 and 220 may adaptively vary with various research and observation demands.

Figure 7A:
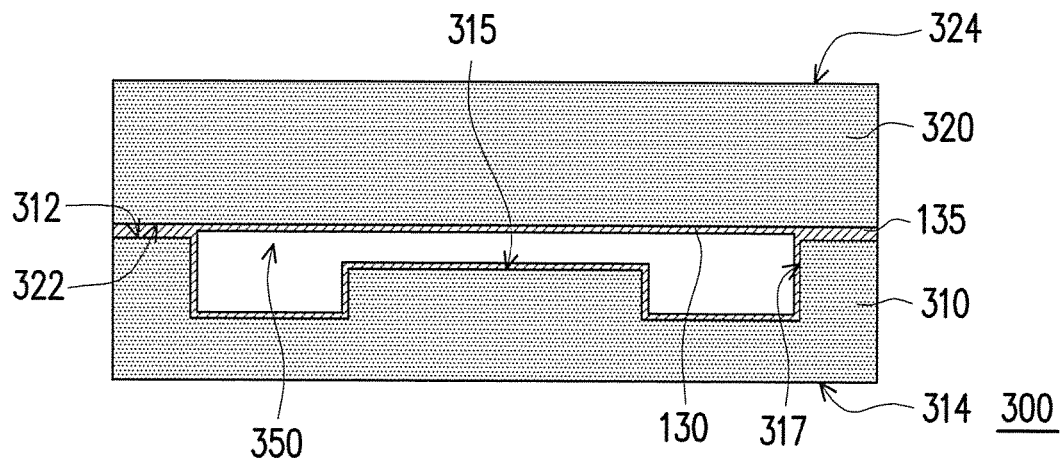
FIG. 7A to FIG. 7C are schematic diagrams illustrating a sample collection device according to another embodiment of the invention.
Figure 7B:
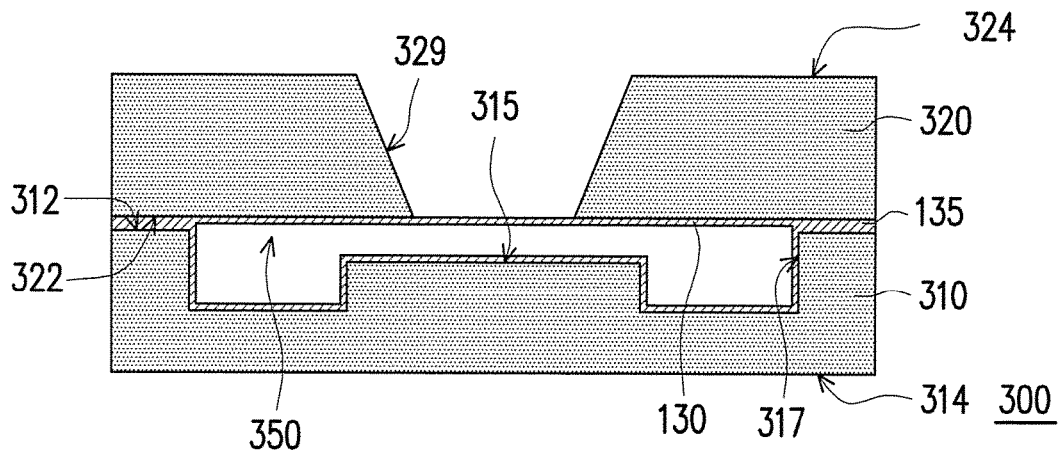
Figure 7C:
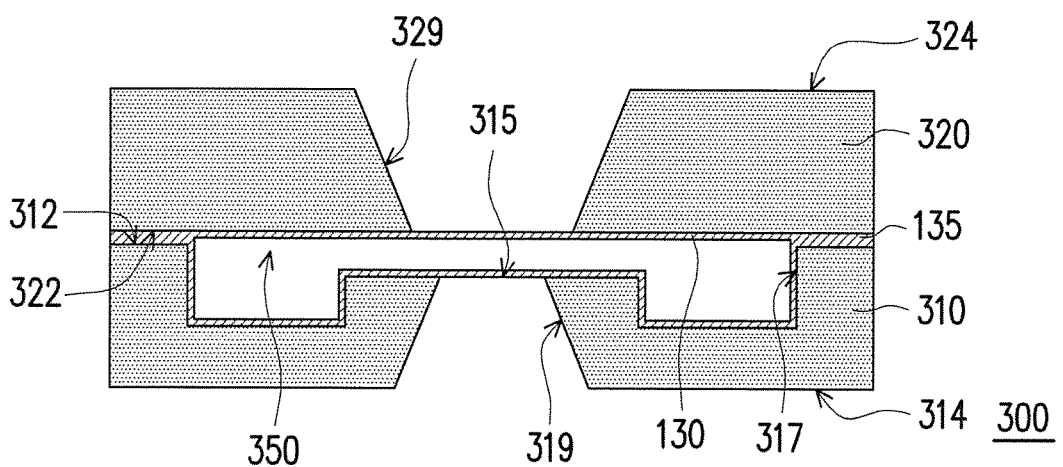

FIG. 7A to FIG. 7C are schematic diagrams illustrating a sample collection device according to another embodiment of the invention. In the present embodiment, a sample collection device 300 has a similar structure to the sample collection device 100, and thus, the same or like elements are labeled by the same or like symbols and will not be repeatedly described. The sample collection device 300 is different from the sample collection devices 100 and 200 of the embodiments above in that a first recess 315 and second recesses 317 are disposed in only one of two substrates 310 and 320 of the sample collection device 300. For example, referring to FIG. 7A, the substrate 310 of the sample collection device 300 has a first surface 312 and a second surface 314, the substrate 320 has a first surface 322 and a second surface 324, and the substrate 310 has a first recess 315 and two second recesses 317 which are respectively disposed at the left and the right sides of the first recesses 315. In addition, when the two substrates 310 and 320 are laminated, two openings of the second recesses 317 at two sides of the substrate 310 may be connected to the outside of the sample collection device 300, such that the liquid solution sample may flow in and out through the two openings of the second recesses 317. Furthermore, no recess is further disposed on the substrate 320 in the present embodiment.

In the present embodiment, the first recess 315 and the second recesses 317 of the substrate 310 are interconnected, which surround together with the substrate 320 and the spacer 135 to form a sample containing space 350. In addition, referring to FIG. 7B, an observation window 329 may be formed in the second surface 324 of the substrate 320. When the sample collection device 300 is applied in, for example, a SEM, a user may observe variation of the liquid solution sample in the sample containing space 350 through the observation window 329.

Referring to FIG. 7C, in the present embodiment, an observation window 319 may also be formed in the second surface 314 of the substrate 310, such that the sample collection device 300 of the present embodiment may be applied to the observation of a TEM. The user may observe the liquid solution sample in the sample containing space 350 from the upper and the lower sides of the sample collection device 300 through the observation windows 319 and 329 in the two substrates 310 and 320.

A possible manufacturing method of the sample collection device 100 of one of the embodiments above will be described below. FIG. 8A to FIG. 8F sequentially illustrate steps for manufacturing a sample collection device according to an embodiment of the invention.

Figure 8A:
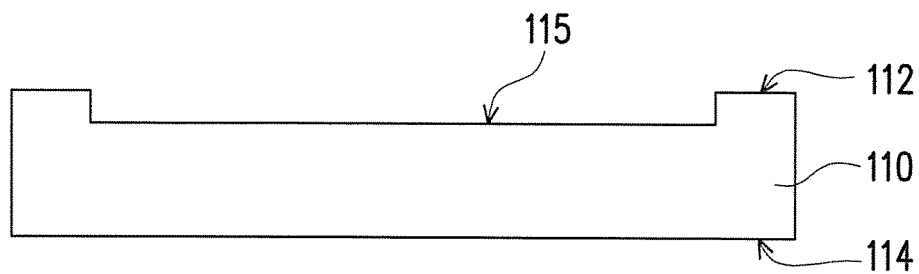
FIG. 8A to FIG. 8F sequentially illustrate steps for manufacturing a sample collection device according to an embodiment of the invention.

First, referring to FIG. 8A, a semiconductor substrate 110 is provided to serve as a substrate, which is, for example, a silicon substrate. In the present embodiment, after an exposure and development step is performed on the semiconductor substrate 110, the first surface 122 of the semiconductor substrate 110 is etched to form the structure of the first recess 115 having a depth about 0.1 μm.

Figure 8B:
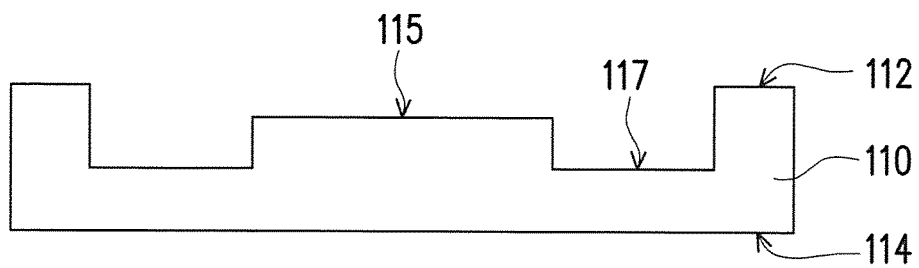

Then, referring to FIG. 8B, after the aforementioned step and the photoresist exposure and development step are performed on the semiconductor substrate 110, the formed first recess 115 is etched to form a deep recess structure having a depth about 5 μm, which is the structure of the second recesses 117.

Figure 8C:
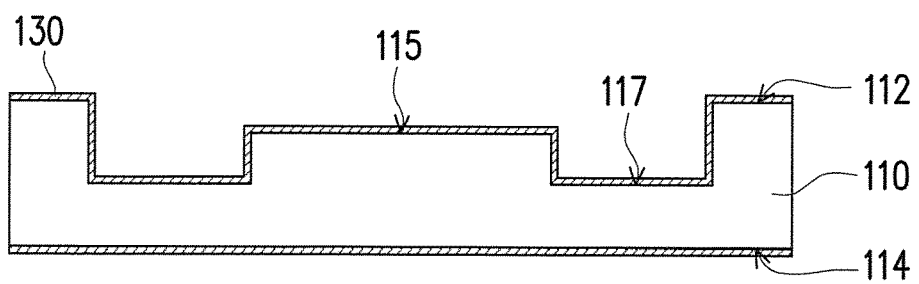

Thereafter, referring to FIG. 8C, the insulation layer 130 having a thickness about 100 nm is deposited on the first recess 115, the second recesses 117 and the second surface 114 of the semiconductor substrate 110 which are formed in the aforementioned steps by a high-temperature chemical reaction process. In the present embodiment, a material used for forming the insulation layer 130 is, for example, a silicon nitride film. Besides, the material of the insulation layer 130 may also be silicon oxide or a composite film jointly composed of silicon nitride and silicon oxide.

Then, referring to 8D, the insulating layer 130 on the second surface 114 of the semiconductor substrate 110 is patterned to define a position of the observation window 119 which is subsequently formed. Subsequently, the manufacturing steps illustrated in FIG. 8A to FIG. 8D are repeatedly performed on another semiconductor substrate 120.

Figure 8D:
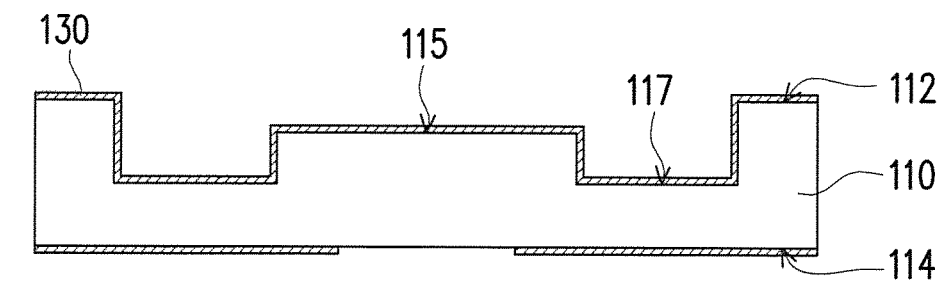
Figure 8E:
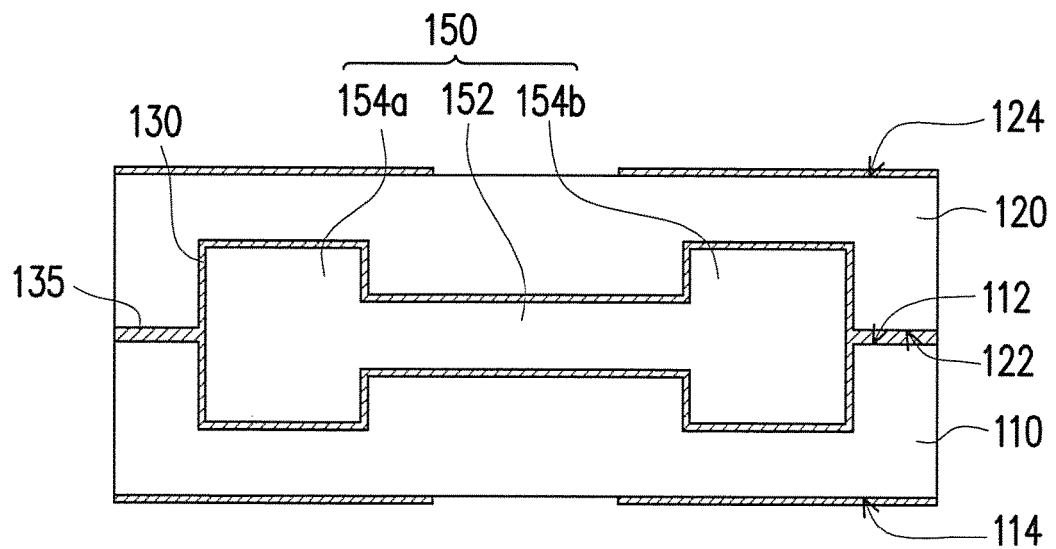

Thereafter, referring to FIG. 8E, after the manufacturing steps performed on the semiconductor substrates 110 and 120 are completed, the two semiconductor substrates 110 and 120 with the formed recess structures are aligned along the structures in the first surfaces 112 and 122 thereof and stacked together, and in the meantime, a high-temperature fusion bonding process is performed on the insulation layer 130, which is a silicon nitride film, on the first surfaces 112 and 122. In the present embodiment, the insulation layer 130 on the first surface 112 of the substrate 110 and the first surface 122 of the substrate 120 may serve as the spacer 135 between the substrate 110 and the substrate 120 after being fused and bonded. In the present embodiment, the sample containing space 150 of the sample collection device 100 may be formed among the first surface 112 of the semiconductor substrate 110, the first surface 122 of the semiconductor substrate 120 and the spacer 135 and includes the first chancel 152 and the two second channels 154a and 154b.

Figure 8F:
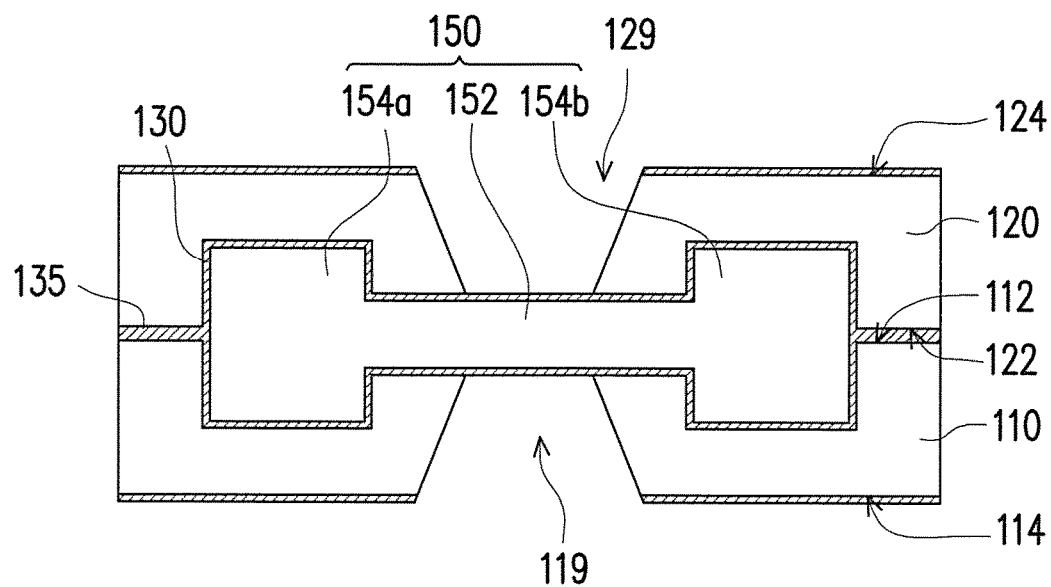

Thereafter, referring to FIG. 8F, the observation windows 119 and 129 are formed by etching the second surface 114 of the semiconductor substrate 110 and the second surface 124 of the semiconductor substrate 120 in a direction toward the sample containing space 150 through, for example, a chemical wet etching or dry etching process, and the insulation layer 130 on part of the first surface 112 and the insulation layer 130 on part of the first surface 122 are respectively exposed.

As such, the sample collection device 100 is substantially manufactured.

Figure 9A:
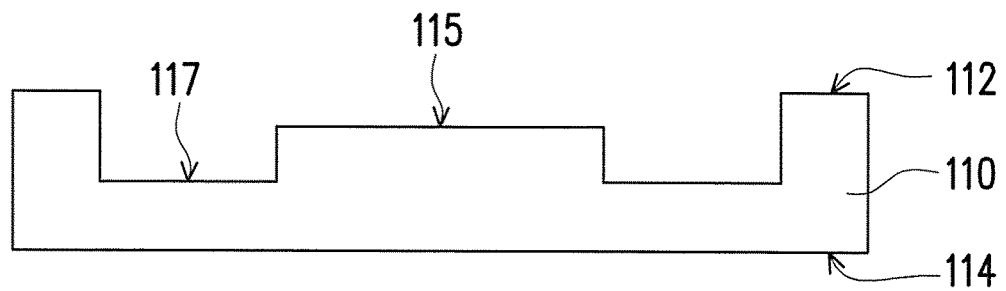
FIG. 9A to FIG. 9G sequentially illustrate steps for manufacturing a sample collection device according to another embodiment of the invention.
Figure 9B:
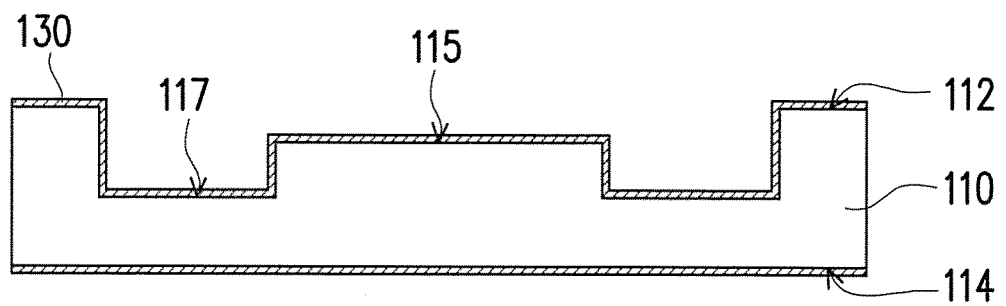
Figure 9C:
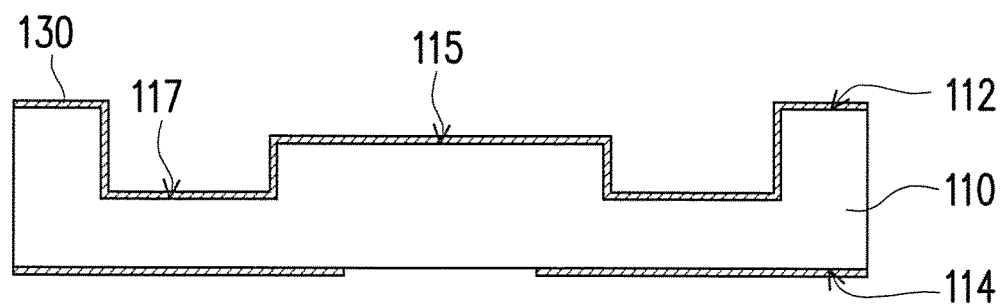
Figure 9D:
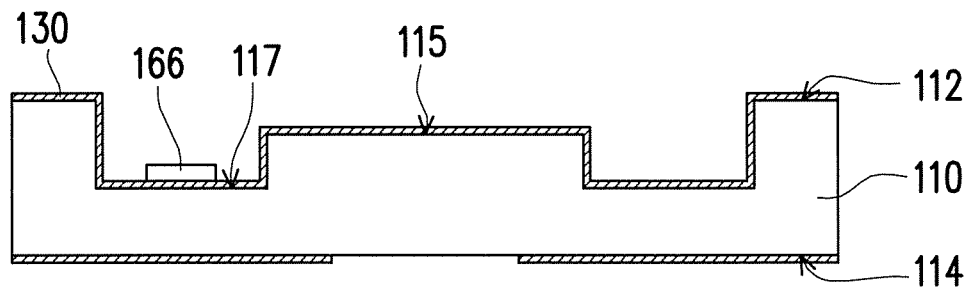

FIG. 9A to FIG. 9G sequentially illustrate steps for manufacturing a sample collection device according to another embodiment of the invention. The manufacturing steps illustrated in FIG. 9A to FIG. 9C are the same as the manufacturing steps illustrated in FIG. 8A to FIG. 8C and thus, will not be repeated. Referring to FIG. 9D, the difference between the step of the present embodiment and that of the preceding embodiment lies in that the heating element 166 is manufactured on the insulating layer 130 on the surface of the second recess 117 of the semiconductor substrate 110 through ion implantation and chemical vapor deposition after the first recess 115, the second recess 117 and the insulation layer 130 of the first surface 122 of the semiconductor substrate 110 are manufactured. In addition, in other embodiments that are not shown, the reaction electrodes or the sensing elements may also be formed in the second recess 117 by the aforementioned manufacturing process.

Besides, the heating elements 166 or the sensing elements may also be formed near the openings at the two ends of the second recess 117. In the present embodiment, the disposition positions for forming the heating elements 166 or the sensing elements 168 may be adaptively changed and adjusted according to actual observation or measurement demands.

Figure 9E:
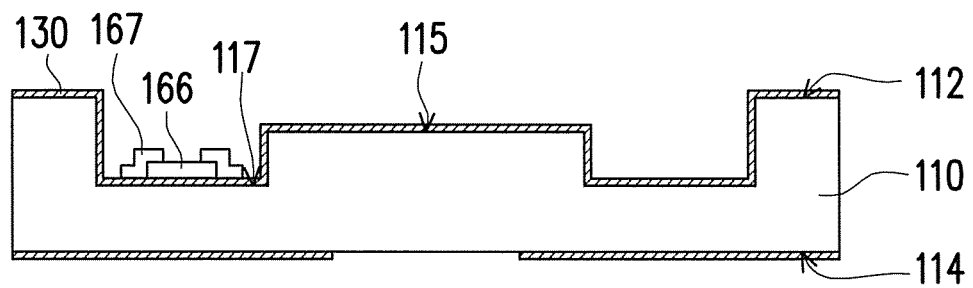

Then, referring to FIG. 9E, a metal wire 167 made of a material, e.g., Ti or Pt, may be manufactured on the heating element 166 by a metal sputtering or a lift-off process. Thereafter, the manufacturing steps illustrated in FIG. 9A to FIG. 8D are repeatedly performed on another semiconductor substrate 120.

Figure 9F:
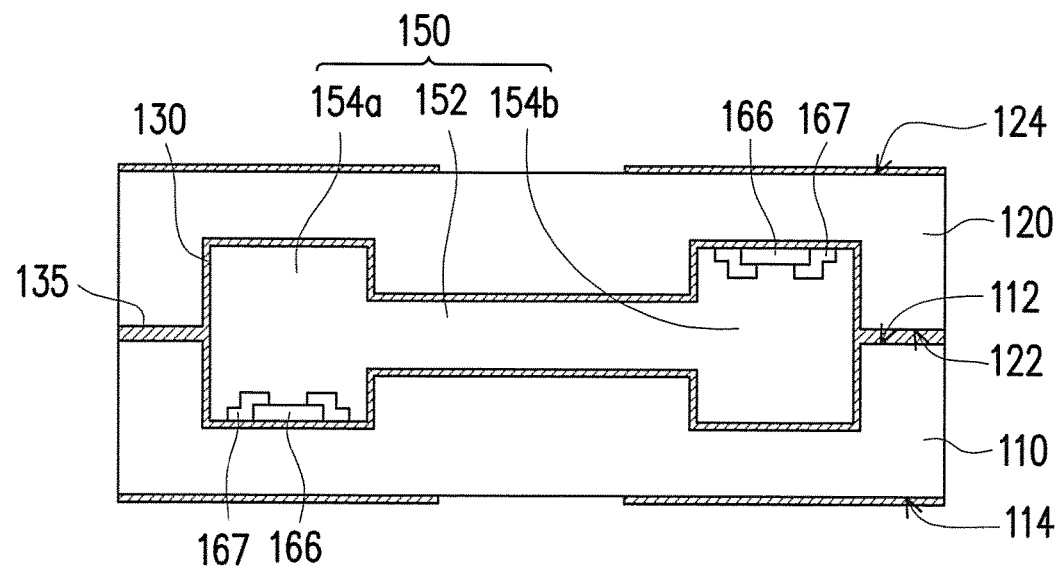

Then, referring to FIG. 9F, the two semiconductor substrates 110 and 120 are bonded by bonding the insulation layer 130 on the first surface 112 and the insulation layer 130 on the first surface 122 through, for example, a high-temperature fusion bonding process, such that the spacer 135 is formed between the first surface 112 of the semiconductor substrate 110 and the first surface 122 of the semiconductor substrate 120 to bond and fix the semiconductor substrate 110 and the semiconductor substrate 120.

Figure 9G:
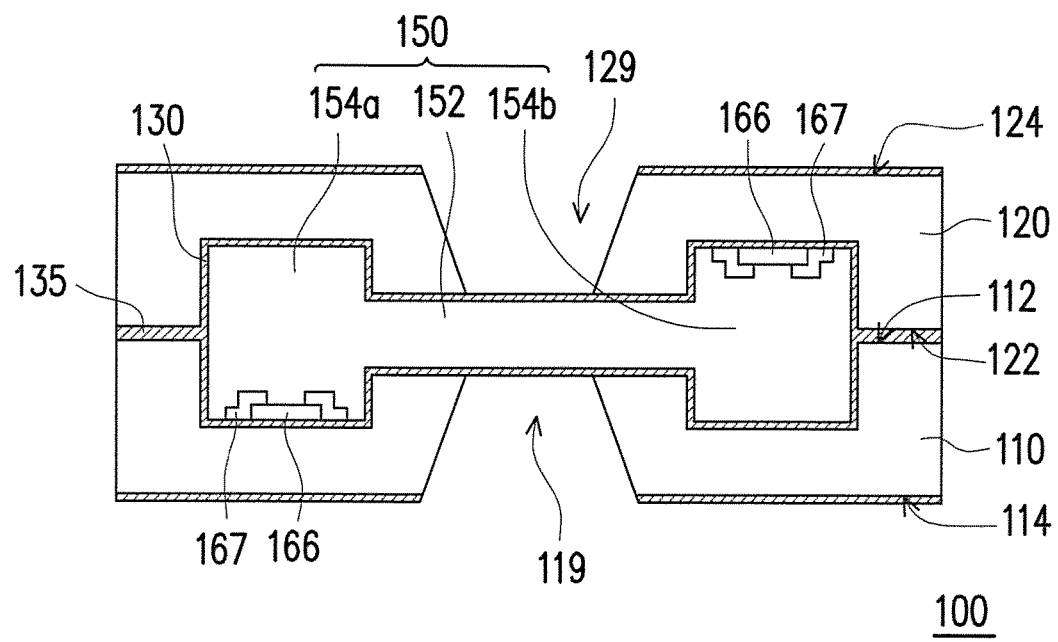

Then, referring to FIG. 9G, the observation windows 119 and 129 are formed by etching the second surface 114 of the semiconductor substrate 110 and the second surface 124 of the semiconductor substrate 120 in a direction toward the sample containing space 150 through, for example, a chemical wet etching or dry etching process, and the insulation layer 130 on part of the first surface 112 and the insulation layer 130 on part of the first surface 122 are respectively exposed. As such, the sample collection device 200 is substantially manufactured.

Based on the above, in the sample collection device provided by the plurality of embodiments of the invention, the sample containing space includes the first channel and the second channels having different heights and sectional areas, and the first channel and the second channels are interconnected. The sample collection device can affect the velocities, the flow directions and the temperatures of the liquid solution sample in the first channel by utilizing the variation of the dispositions manners of the second channels located at two sides of the first channel and the changes of the temperatures, velocities and flow directions of the liquid solution sample flowing through the first channel. Therefore, the sample collection device of the invention can be applied to observe the flow field mode of the particles of the liquid solution sample in different velocities and flow directions or physical or chemical changes in different temperatures. Thereby, the sample collection device may achieve effectively controlling the flow directions, velocities and temperatures of the liquid solution sample in the sample containing space through the disposition of the first channel and the second channel. Moreover, in the sample collection device provided by the plurality of embodiments of the invention, reaction electrodes, heating elements or sensing elements can be disposed in the sample containing space, such that the sample collection device according to the plurality of embodiments of the invention can widely applied in various aspects of liquid sample observations. Furthermore, the sample containing space of the sample collection device of the invention is not formed by additionally depending on the components of the electron microscope, and thus, when the observation of the sample is completed, and the sample is to be changed, the sample collection device provided according to the embodiments of the invention can be entirely removed from the electron microscope, such that the sample collection device provided by the plurality of embodiments of the invention can be commonly used in different types of microscopes.

Although the invention has been disclosed by the above embodiments, they are not intended to limit the invention. It will be apparent to one of ordinary skill in the art that modifications and variations to the invention may be made without departing from the spirit and scope of the invention. Therefore, the scope of the invention will be defined by the appended claims.

What is claimed is:

1. A sample collection device, comprising:
   two substrates, disposed oppositely to each other, wherein each of the substrates has a first surface, a second surface opposite to the first surface, a first recess and at least one second recess, the two substrates are disposed with the first surfaces facing each other, the first recess and the at least one second recess are respectively sunk into the first surface and collectively channeled through the each of the substrates, the first recess and the at least one second recess are spatially interconnected and fluidly communicated with each other, the first recesses of the substrates jointly form a first channel, the second recesses of the substrates jointly form at least one second channel connected to the outside of the sample collection device, and the first channel and the at least one second channel are interconnected,
   wherein the surfaces of the first recess and the at least one second recess of each of the substrates are fully covered by an insulation layer; and
   a spacer, disposed between the two first surfaces to bond and fix the two substrates, wherein a sample containing space is formed between the two substrates and the spacer, and the sample containing space comprises the first channel and the at least one second channel.

2. The sample collection device according to claim 1, wherein the first channel and the at least one second channel respectively have a first depth and a second depth, and the second depth is greater than the first depth.

3. The sample collection device according to claim 2, wherein the first depth ranges from 0.01 μm to 10 μm.

4. The sample collection device according to claim 2, wherein the second depth ranges from 0.1 μm to 400 μm.

5. The sample collection device according to claim 1, wherein each of the substrate comprises an observation window, the observation window is disposed on the second surface and corresponding to the first channel of the sample containing space.

6. The sample collection device according to claim 1, further comprising an inlet and an outlet, wherein the inlet is located in an opening at one end of one of the first channel and the at least one second channel, and the outlet is located in an opening at the other end of one of the first channel and the at least one second channel.

7. The sample collection device according to claim 1, further comprising an inlet and an outlet, wherein the inlet is located in an opening at one end of the at least one second channel, and the outlet is located in an opening the other end of the at least one second channel.

8. The sample collection device according to claim 1, wherein the number of the at least one second channel is two, and a longitudinal extension direction of the second channels is parallel to a longitudinal extension direction of the first channel.

9. The sample collection device according to claim 8, wherein two ends of each of the second channels respectively have an inlet and an outlet, and the inlet of one of the second channels and the outlet of the other second channel are located at the same side.

10. The sample collection device according to claim 8, wherein one of the substrates has an inlet located on the second surface of the substrate, and the inlet is connected with one of the second channels, and the other substrate has an outlet located on the second surface of the substrate, and the outlet is connected with the other second channel.

11. The sample collection device according to claim 8, wherein one of the substrates has an inlet and an outlet, and the inlet and the outlet are respectively located on the second surface of the substrate and respectively connected with at least one of the second channels.

12. The sample collection device according to claim 1, further comprising: at least one set of reaction electrodes disposed in the first channel.

13. The sample collection device according to claim 1, further comprising: at least one set of heating elements or sensing elements disposed in the at least one second channel.

14. The sample collection device according to claim 1, further comprising: at least one set of heating elements or sensing elements disposed near an opening at one end of the at least one second channel.

15. A sample collection device, comprising:
two substrates, disposed oppositely, wherein each of the substrates comprises a first surface and a second surface opposite to the first surface, one of the substrates has a first recess and at least one second recess, the first recess and the at least one second recess are respectively sunk into the first surface and collectively channeled through the each of the substrates, the first recess and the at least one second recess are spatially interconnected and fluidly communicated with each other, the at least one second recess is connected to the outside of the sample collection device, the two substrates are disposed with the two first surfaces facing each other, and the first channel and the at least one second channel are interconnected,
wherein the surfaces of the first recess and the at least one second recess of each of the substrates are fully covered by an insulation layer; and
a spacer, disposed between the two first surfaces to bond and fix the two substrates, wherein a sample containing space is surrounded by and formed between the two substrates and the spacer.

16. The sample collection device according to claim 15, wherein at least one of the two substrates has an observation window disposed on the second surface and corresponding to the first recess.

* * * * *